US00PP07796P

United States Patent [19]

Drewlow

[11] Patent Number: Plant 7,796

[45] Date of Patent: Feb. 18, 1992

[54] IMPATIENS PLANT NAMED ILLUSION

[75] Inventor: Lyndon W. Drewlow, Ashtabula, Ohio

[73] Assignee: Mikkelsens, Inc., Ashtabula, Ohio

[21] Appl. No.: 607,379

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A new and distinct cultivar of Impatiens plant named Illusion, characterized by its large, rose pink flowers with distinct carmine eye and flesh pink area outside the eye; long spur on mature flower bud; large dark green leaves with purplish cast, no variegation and red venation; early blooming habit; two flower buds per leaf axil; deep red stem coloration; floriferous habit; and its ability to continuously bloom under both high and low temperatures and high sunlight.

1 Drawing Sheet

The present invention comprises a new and distinctive cultivar of Impatiens plant, botanically known as Impatiens, and known by the cultivar name Illusion. The new cultivar was developed by me through controlled breeding by crossing Mikkelsen Seedling No. 84-1396-5 (seed parent) with Mikkelsen Seedling No. 86-412-19 (pollen parent).

Asexual reproduction by terminal or stem cuttings has shown that the unique features of this new impatiens are stabilized and are produced true to type in successive propagations.

The following combination of characteristics distinguish Illusion from both its parent varieties and other cultivated impatiens of this type known and used in the floriculture industry, including the comparison cultivars referred to, namely, Columbia (U.S. Plant Pat. No. 5,126) and Dawn (U.S. Plant Pat. No. 5,775).

Color references are to the Royal Horticultural Society Colour Chart (R.H.S.).

1. Illusion has rose pink flower color (50B to 50C) with a distinct carmine eye (51A), while Columbia and Dawn are more lavender pink (62A) and salmon pink (48C), respectively.

2. Illusion has a larger flower, averaging 6.5 to 7 cm in diameter, while Dawn and Columbia have smaller flowers averaging 5 to 6 cm in diameter.

3. Illusion has a longer spur (6.0 cm) on a mature flower bud while the spur of Columbia is 5.0 cm and the spur of Dawn is the shortest at 3.0 to 3.5 cm.

4. Illusion has an area outside the carmine eye that is flesh pink and extends out into the petals. The color is similar to Dawn but the area of Dawn is more restricted to the center of the flower. Columbia does not have a flesh pink area at the center of the flower.

5. Illusion has stigmas and styles that are white with reddish tint in color, while Columbia and Dawn have white stigmas and styles.

6. Illusion has an ovary that is green with a reddish-purple cast, while both Columbia and Dawn both have a bright green ovary.

7. Illusion has dark green leaves with a purplish cast and no variegation, while both Dawn and Columbia have bright green leaves with cream variegation at the base and midrib of the leaves.

8. Illusion has larger leaves at 10 to 11 cm long and 4.0 to 4.5 cm wide, with Columbia having leaves which are 7-8 cm long and 2.5 to 3.0 cm wide, and Dawn having the smallest leaves at 4 to 5 cm long and 2.25 to 2.5 cm wide.

9. Illusion has red venation in the leaves, while both Dawn and Columbia have green venation.

10. Illusion is 7 to 10 days earlier to bloom than either Columbia or Dawn.

11. Illusion usually has two flower buds per leaf axil, while Dawn and Columbia have only one.

12. Illusion has the deepest red coloration of the stem, with Dawn having only a pinkish cast and Columbia being intermediate in red coloration of the stem.

The accompanying colored photograph illustrates in front perspective view the overall appearance of Illusion showing the colors as true as reasonably possible to obtain in a colored reproduction of this type. The photo was taken on Dec. 20, 1989 under natural light on an overcast day under double poly greenhouse covering at Ashtabula, Ohio.

The following is a detailed description of Illusion, based on plants produced in greenhouses in Ashtabula, Ohio during the summer season of the year. Plants were grown in 15 cm pots and measurements were taken 16 weeks after rooted cuttings were planted. Height measurements were taken from the soil line of the container. The plants were grown at 65°-68° F. night temperatures, under 3500 to 4500 foot candles of light, and 240 ppm nitrogen, 240 ppm potassium, and 175 ppm phosphorous nutritional levels with trace elements added. Habit of growth, foliage coloration, leaf variegation, size of leaves and flower size will be greatly influenced by nutritional and environmental conditions. Color references are made to the Royal Horticultural Society Colour Chart (R.H.S.) except where general terms of ordinary dictionary significance are used.

Parentage: A controlled cross between female Mikkelsen Seedling No. 84-1396-5 and male Mikkelsen Seedling No. 86-412-19.

Propagation:

A. *Type cutting.*—Stem tip 15 mm long will develop to 4 to 5 cm long in 18 to 21 days.

B. *Time to initiate roots.*—8-10 days at 23° C. summer; 10-12 days at 20° C. winter.

C. *Rooting habit.*—Heavy, fibrous.

Plant description: Habit of growth, foliage coloration and size of leaf will be greatly influenced by nutritional and environmental conditions. Thus, data that follows was taken from plants grown under the conditions stated above.

A. *Form and habit of growth.*—Mounded; highly self-branched; semi-tall in height; flowers over the top of leaf canopy; continuous flowering; vigorous growing flowering herb.

B. *Foliage description.*—Yellow green leaves with reddish-purple cast to midrib; no leaf variegation; reddish-purple cast to bottom of leaf. 1. Size: 10 to 11 cm long and 4.0 to 4.5 cm wide for the average mature leaf. 2. Shape: Lanceolate to ovate with acuminate apex. 3. Texture: Both upper and lower surfaces are glabrous. 4. Margin: Slightly serrated with fine ciliate. 5. Color: Young foliage top side, 146A; under side 146B with 183D cast. Mature foliage top side 146A; under side 146B with 183D cast. 6. Venation: Pinnate; red in color.

Flowering description:

A. *Flowering habits.*—Flowers continuously from leaf whorl in a progressively orderly manner with two flowers per leaf axil. All first flowers in a whorl open before the second flower in the leaf axil of that whorl start to open. When the second flower in a leaf axil opens the first flower in the leaf whorl above start to open. It takes 5 to 7 days for a mature bud to fully open, with the flowers lasting two weeks or longer depending on the environment.

B. *Natural flowering season.*—Indeterminant and continuous. Quantity of flowering increases with increasing levels of light.

C. *Flower buds.*—Ellipsoidal, flowers perfect; reddish spur (6.0 cm) on mature bud with green tip; throat behind ovary and originating from major sepal.

D. *Flowers borne.*—Individual reddish pedicels develop from a whorl of 5 to 6 leaves, flowering progressively around the whorls as buds and leaves develop. Leaf axils usually have two flower buds.

E. *Quantity of flowers.*—Because of highly self-branching nature of cultivar, long lasting flowers, and two flowers per leaf axil. Illusion is very floriferous. Flower development is continuous and above the leaf canopy.

F. *Diameter of flower.*—6.5 to 7.0 cm.

G. *Petals.*—1. Shape: Heart-shaped; standard is largest petal. 2. Color: Top side when opening 50B to 50C with areas near center as light as 49C; eye at center 51A; fading to 50D to 49C. Under side, 48D. 3. Number of petals: Five. 4. Size of petals: Standard — 3.0 cm long by 4.0 cm wide; two equal lobes, shallow cut. Wings — 3.3 cm long by 3.0 cm wide; two unequal lobes, moderate cut. Keel — 3.0 cm long by 3.5 cm wide; two equal lobes, moderate cut.

Reproductive organs:

1. *Stamens.*—Five in number. Anther shape is hooded; white in color with reddish tint. Pollen color is cream.

2. *Pistils.*—Stigma shape is five segmented column; white with reddish tint in color. Style color is white with reddish tint. Ovaries, five in number; 5 mm in size; color is green with reddish-purple cast.

Disease resistance: No significant disease and insect problems to date.

OTHER IMPORTANT CHARACTERISTICS

1. Illusion has shown the ability to tolerate both high temperatures and sunlight and continue to bloom, as well as cool temperatures (40°-50° F.). Thus, growing season outdoors has been extended.

2. Self-branching, early flowering nature allows this cultivar to be grown in 10 cm pots but Illusion is also vigorous so it can be grown in 15 to 25 cm containers.

3. Illusion has a mounded to semi-upright growth habit, while Columbia is upright growing and Dawn is more compact and mounded in growth.

I claim:

1. A new and distinct cultivar of Impatiens plant named Illusion, as illustrated and described.

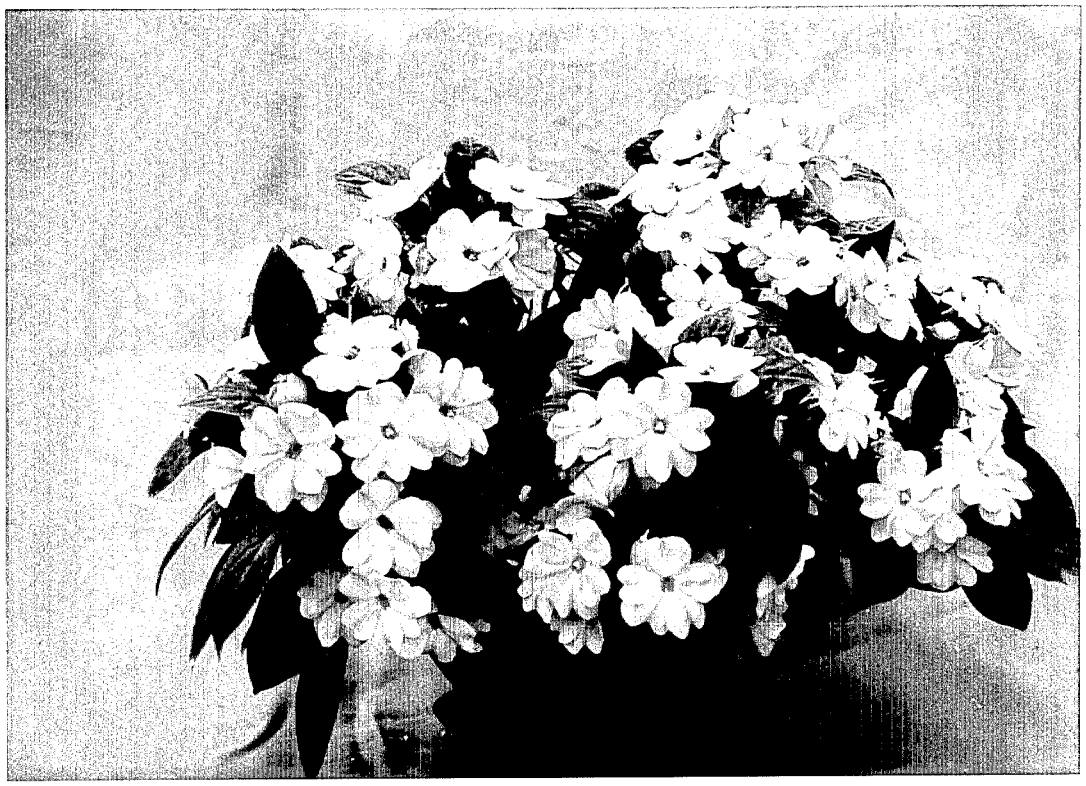

* * * * *